United States Patent [19]
Holscher

[11] Patent Number: 5,443,075
[45] Date of Patent: Aug. 22, 1995

[54] FLOW MEASURING APPARATUS

[75] Inventor: Russell L. Holscher, Olathe, Kans.

[73] Assignee: Puritan-Bennett Corporation, Lenexa, Kans.

[21] Appl. No.: 25,045

[22] Filed: Mar. 1, 1993

[51] Int. Cl.⁶ ............................................. A61B 5/087
[52] U.S. Cl. .................................. 128/725; 73/861.42
[58] Field of Search ...................... 128/725; 73/861.42, 73/861.52, 861.65, 861.66, 861.67

[56] References Cited

U.S. PATENT DOCUMENTS

| | | | |
|---|---|---|---|
| 3,312,106 | 4/1967 | Davis | 73/861.42 |
| 4,047,521 | 9/1977 | Kramer et al. | 128/725 |
| 4,896,541 | 1/1990 | Hughes | 73/861.52 |

FOREIGN PATENT DOCUMENTS 0888937 12/1981 U.S.S.R. ............... 128/725

OTHER PUBLICATIONS

Frank M. White, McGraw-Hill, Inc., 1979, Table 72, "Fluid Mechanics".

Puritan-Bennett, 1991, 2.1–2.23, "Companion 318 Nasal CPAP System" (Service Manual).

Puritan-Bennett, Oct. 1992, 15–18, "Companion 318 Nasal CPAP System" (Clinical Manual).

*Primary Examiner*—Lee S. Cohen
*Attorney, Agent, or Firm*—Fulwider Patton Lee & Utecht

[57] ABSTRACT

Apparatus for accurately and reliably measuring fluid flow under turbulent or pulsating conditions with high signal-to-noise ratio and using a symmetrical design which works with flow in either direction. The apparatus is particularly well-suited for measuring airflow in a bi-level respiratory system. The apparatus includes a flow conduit, an upstream sense tube protruding into the flow conduit with a notch opening facing into the flow stream, a downstream sense tube protruding into the flow conduit with a notch opening facing away from the flow stream, and a flow or pressure sensor/-transducer disposed in connecting lines between the upstream and downstream sense tubes. The notched opening has a semi-cylindrical shape. The flow conduit is either straight or angled.

18 Claims, 4 Drawing Sheets

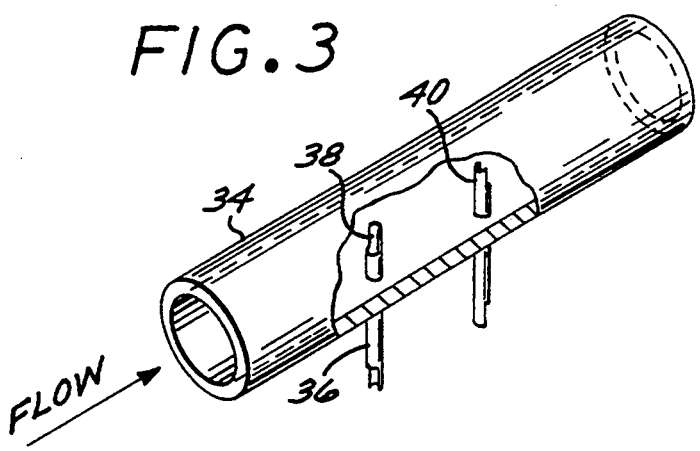
FIG.3
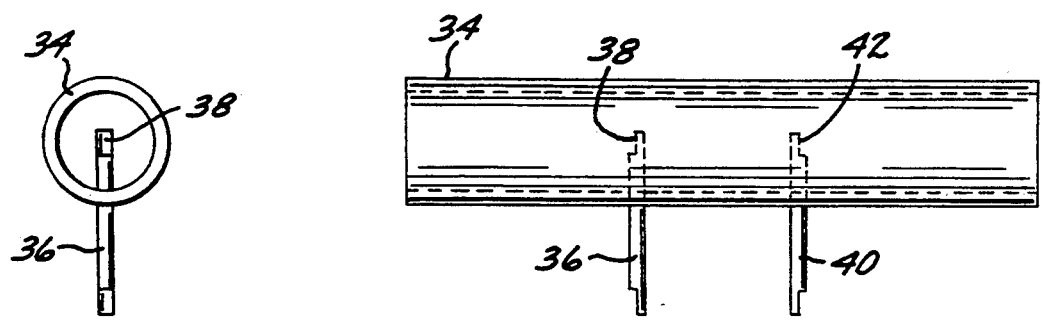
FIG.4
FIG.5

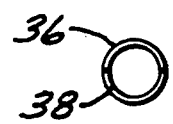
FIG. 9
FIG. 6  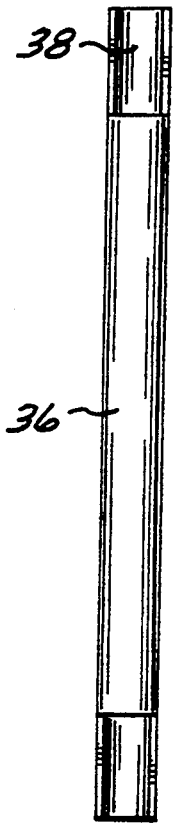 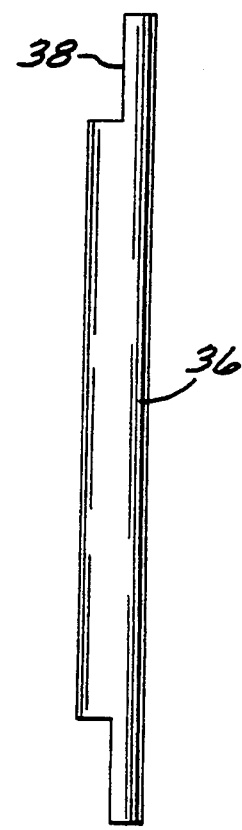
FIG. 7  FIG. 8

FIG. 11
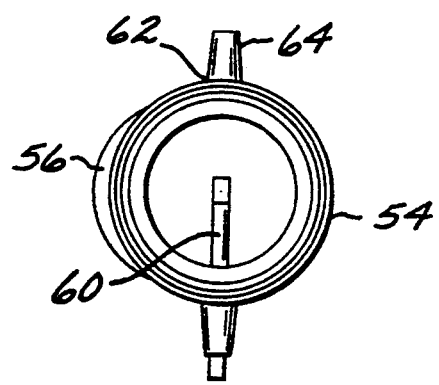
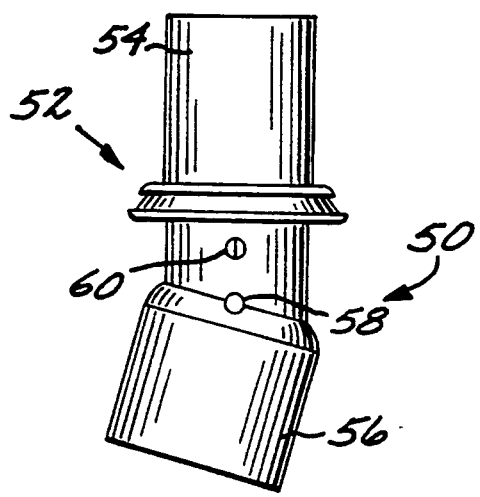
FIG. 10

FLOW MEASURING APPARATUS

BACKGROUND OF THE INVENTION

1. Field of the Invention

This invention relates generally to improvements in apparatus for the measurement of fluid flow and, more particularly, to a new and improved apparatus for measuring gas flow in a respiratory therapy system for the treatment of sleep apnea and other breathing disorders.

2. Description of the Prior Art

There are numerous applications in modern engineering practice that require the measurement of fluid flow. Over time, tubes of various sizes and shapes have been designed and constructed for this purpose.

The first description of a tube used to measure fluid pressures for velocity determinations is credited to Henri Pitot, and tubes for this purpose have frequently been named after him. Today, there are many different arrangements and geometrical shapes of Pitot tubes adapted for a wide variety of applications.

A typical Pitot tube arrangement consists of a cylindrical tube with an open end located in the fluid flow stream and pointed upstream to measure stagnation or impact pressure (where the stream is decelerated to zero velocity), plus one or more sidewall taps in the flow conduit to measure local static pressure in the moving stream. The difference between the impact pressure and the static pressure is a function of the velocity of the flow stream.

Upstream disturbances in the fluid flow stream have a tendency to cause large errors in the flow measurement, in part because of the turbulence generated and its effect on the static pressure measurement. A calming section of a least several pipe diameters or more is often utilized to obtain accurate measurements. Pulsating flow also can have an adverse effect on flow measurement accuracy, to the extent that damping mechanisms are sometimes used to avoid significant measurement errors.

Flow measuring devices are commonly used in a wide variety of modern medical systems. One type of such system is a respirator used for the treatment of obstructive sleep apnea.

Obstructive sleep apnea is a sleeping disorder characterized by relaxation of the airway including the genioglossus throat muscle during sleep. When this occurs the relaxed muscle can partially or completely block the patient's airway. Partial blockage can result in snoring or hypopnea. Complete blockage results in obstructive sleep apnea.

When complete blockage occurs, the patient's inhalation efforts do not result in the intake of air and the patient becomes oxygen deprived. In reaction, the patient begins to awaken. Upon reaching a nearly awakened state, the genioglossus muscle resumes normal tension which clears the airway and allows inhalation to occur. The patient then falls back into a deeper sleep whereupon the genioglossus muscle again relaxes in the apneic cycle repeats. In consequence, the patient does not achieve a fully relaxed deep sleep session because of the repetitive arousal to a nearly awakened state. People with obstructive sleep apnea are continually tired even after an apparently normal night's sleep.

In order to treat obstructive sleep apnea, a system of continuous positive airway pressure (CPAP) has been devised in which a prescribed level of positive airway pressure is continuously imposed on the patient's airway. The presence of such positive pressure provides a pressure splint to the airway in order to offset the negative inspiratory pressure that can draw the relaxed airway tissues into an occlusive state.

The most desired device for achieving a positive airway connection is the use of a nasal pillow such as that disclosed in U.S. Pat. No. 4,782,832, hereby incorporated by reference. The nasal pillow seals with the patient's nares and imposes the positive airway pressure by way of the nasal passages. The nasal pillow also includes a small vent for continuously exhausting a small amount of air in order prevent carbon dioxide and moisture accumulation.

In the CPAP system, the patient must exhale against the prescribed positive pressure. This can result in patient discomfort, especially at the higher pressure levels. Because of this problem, the so-called bi-level positive airway pressure (BiPAP) system has been developed in which the pressure is lowered during the exhalation phase of the respiratory cycle.

In a BiPAP system, air flow to the patient is measured by a flow measuring device pneumatically coupled to the nasal pillow. The measuring device is connected to a flow sensor with a transducer to produce an electrical signal representative of the air flow delivered to the patient. The signal is used by electronic circuitry to control the pressure of the respiratory gas being delivered to the patient. A pressure sensor also is used to provide the circuitry with a signal representative of the pressure being delivered to the patient.

These types of respirator systems can experience turbulent and pulsating flow in the delivered stream of respiratory gas. Turbulence is often the result of bends in the flow path and insufficient space to provide for calming sections to return to laminar flow. Additionally, under certain conditions, the direction of flow can reverse itself, causing problems for uni-directional flow sensors.

It is apparent that accurate measurement of the air flow provided to the patient is an important feature in a respirator system. Ideally, the measurement should accurately reflect the dynamics in a bi-directional flow system and should be accomplished in a manner that provides a high signal-to-noise ratio in both turbulent and laminar flow regimes. The flow measurement also should have linear characteristics with proportionality to the total flow in the system.

Design constraints sometimes require that the flow measurement be determined in a limited space with negligible resultant pressure drop. It is also sometimes desirable that the flow measurement apparatus be incorporated within other parts of the system to reduce the total number of parts. This should be accomplished in a manner which promotes ease of manufacture at low cost.

The traditional Pitot tube employed in previous respirator designs used a right angled tube with an opening directed toward the incoming flow stream and a second right angled tube with an opening directed away from the flow stream. A side flow was developed when these two tubes were immersed in a conduit containing the air flow stream. This side flow was routed to a sensor/transducer. The sensor developed a signal which in turn was conditioned to accurately reflect the total flow output of the system.

While these existing respirator flow measuring devices have served their purpose, there remains a continuing desire for further improvement therein. In particular, a need exists for an improved flow measuring device which enables more accurate and reliable measurements to be made in turbulent or pulsating flow, with high signal-to-noise ratio, and which works well with flow in either direction. The present invention fulfills all of these needs.

SUMMARY OF THE INVENTION

Basically, and in general terms, the present invention provides a new and improved flow measuring apparatus for accurately and reliably measuring fluid flow, particularly under turbulent or pulsating flow conditions, and provides a distinct advance in the state of the art described above. More particularly, the apparatus reliably measures fluid flow with high signal-to-noise ratio using a symmetrical design which works with flow in either direction.

In the preferred embodiment, the present invention provides flow measuring apparatus which is particularly well suited for measuring air flow in a bi-level respirator system. In that application, the invention provides a flow measuring device which substantially reduces the effect of disturbances and pulsating flow on the accuracy of the flow measurement, and which significantly increases the effective signal-to-noise ratio.

More specifically, and in a presently preferred embodiment, by way of example and not necessarily by way of limitation, the flow measuring apparatus embodying various features of the present invention includes a flow conduit, an upstream sense tube protruding into the flow conduit and having a notch opening facing into the flow stream, a downstream sense tube protruding into the flow conduit and having a notch opening facing away from the flow stream, and a flow sensor/transducer disposed in connecting lines between the upstream and downstream sense tubes for producing an electrical signal representative of the side flow therethrough and thereby representative of the total flow of gas in the flow conduit.

In an alternative embodiment, a differential pressure sensor/transducer is disposed in the connecting lines between the upstream and downstream sense tubes in place of the flow sensor for measuring a pressure drop between the sense tubes proportional to flow velocity and thus to the total flow of air delivered through the flow conduit.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 3 is a perspective view, partly cut away, of the flow-conduit and upstream and downstream sense tubes of FIG. 2, with the connecting tubing and flow sensor removed for illustration;

FIG. 4 is a side elevation of the apparatus of FIG. 3;

FIG. 5 is an end view of the apparatus of FIG. 4;

FIG. 6 is an enlarged perspective view of one of the sense tubes of FIG. 3, removed from the flow conduit for illustration;

FIG. 7 is an enlarged front elevational view of the sense tube of FIG. 6;

FIG. 8 is a side elevational view of the sense tube of FIG. 7;

FIG. 9 is an end view of the sense tube of FIG. 7;

FIG. 10 is a plan view of another embodiment of the invention in the form of flow measuring apparatus utilizing an angled flow conduit; and FIG. 11 is an end view of the apparatus of FIG. 10, looking down from the top of FIG. 10.

DESCRIPTION OF THE PREFERRED EMBODIMENTS

Figure 1:
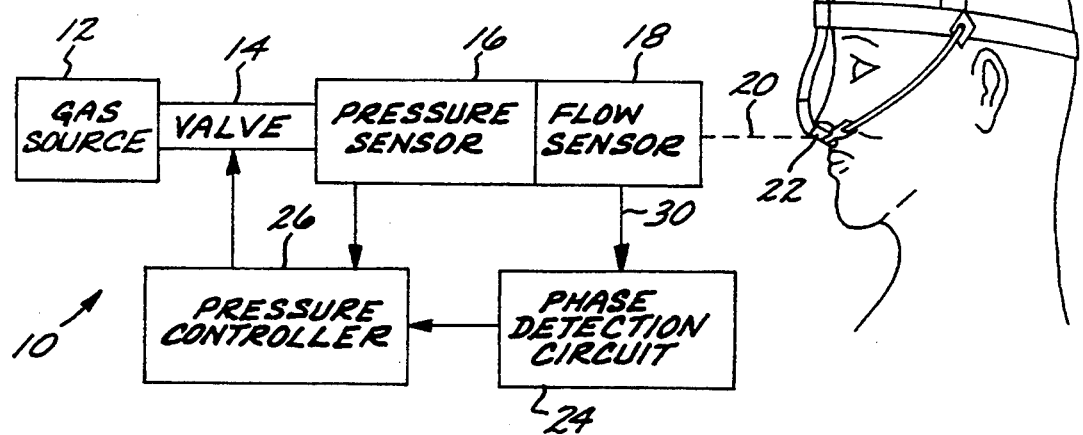
FIG. 1 is a schematic representation of a single or bi-level respiratory system for facilitating the respiration of a patient.

Referring now to the drawings, and more particularly to FIG. 1, the preferred embodiment of invention preferably is utilized in a patient respiratory system 10 of the type including a gas source 12, a control valve 14, a pressure sensor 16 and a flow sensor 18 coupled with a so-called ADAM circuit available from Puritan-Bennett Corporation of Lenexa, Kans., which includes a pneumatic hose 20 and a nasal pillow 22. The system 10 further includes a phase detection circuit 24 and a pressure controller 26. In the preferred embodiment, the components 12–18 and 24–26 are enclosed in a single housing to which the ADAM circuit is coupled.

The gas source 12 typically includes a variable speed blower operable to produce a supply respiratory gas on the order of 120 liters per minute at 30 cm water pressure. The preferred pressure sensor 16 is available from Sensym Company as Model SCX01. The preferred flow sensor 18 is Model AWM2300V available from Microswitch Corp., and includes a transducer operable for producing an electrical signal on line 30 representative of the air flow through the sensor and thereby representative of the air flow in the pneumatic circuit connected to the patient.

The phase detection circuit 24 produces a logic high output during exhalation and a logic low output during inhalation. The controller 26 receives the output signals from the phase detection circuit 24 and also the output from the pressure sensor 16 and, in response, operates the valve 14 to maintain the respective inhalation and exhalation pressures delivered to the patient from the gas source 12.

A more detailed description of the respiratory system and its associated circuity is contained in a commonly assigned patent application entitled "Inhalation/Exhalation Respiratory Phase Detection Circuit", by Stephen L Phillips, Ser. No 08/003,129, filed Jan. 12, 1993, the disclosure of which is incorporated herein by reference.

Figure 2:
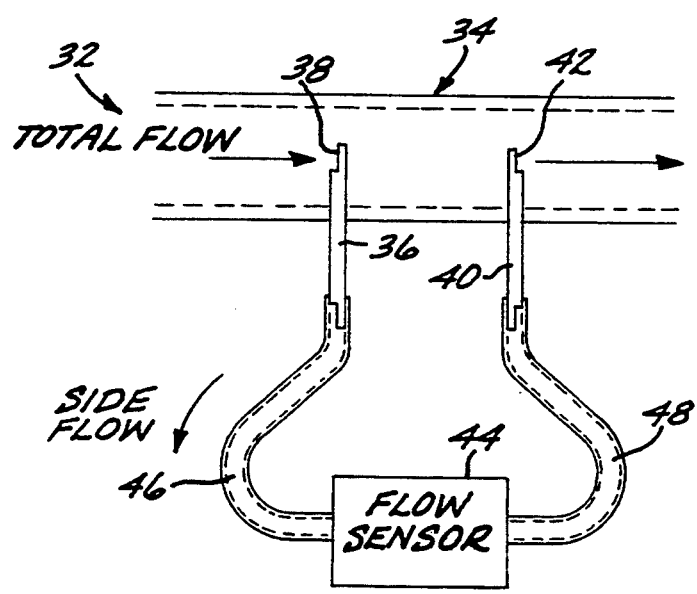
FIG. 2 is a schematic diagram of a flow measuring system embodying some of the novel features of the present invention.

In accordance with one embodiment of the present invention, the flow sensor 18 of FIG. 1 cooperates with the flow measuring device 32 of FIG. 2, to sense and measure the total flow of gas from the gas source 12 through the valve 14 to the patient, and vice versa.

The flow measuring device 32 includes a straight cylindrical flow conduit 34 disposed in the flow path between the output of the control valve 14 and the input to the pneumatic hose 20. The flow conduit 34 may be in the form of a pipe or tube, as illustrated in FIGS. 3–5.

An upstream sense tube 36 protrudes into the flow stream through a first sidewall tap in the flow conduit 34. An interference fit secures the tube 36 in place. The internal end of the tube 36 has a semi-cylindrical notch opening 38 formed therein located in approximately the middle of the flow stream and facing directly into the stream. The external end of the sense tube 36, which extends outside the flow conduit 34, has a similarly configured end geometry. An identical downstream sense tube 40 extends into the flow stream through a second sidewall tap in the flow conduit 34 downstream of the first sidewall tap, and is held in place by an interference fit. The downstream tube 40 has a similar notch opening 42 on the internal end disposed in approximately the middle of the flow stream but facing directly away from the direction of flow through the conduit 34. The external end of the downstream sense tube 40 has a similar end geometry. The notch openings in the external ends of the upstream and downstream sense tubes 36, 40 face upstream and downstream, respectively. These features are best shown in FIGS. 2-5.

Referring again to FIG. 2, the external end of the upstream sense tube 36 is connected to the input or high pressure side of a flow sensor/transducer 44 by a connecting tube 46. The output or low pressure side of the flow sensor/transducer 44 is connected to the external end of the downstream sense tube 40 by another connecting tube 48. Both connecting tubes preferably are formed of silicone. This arrangement produces a side flow of respirator gas through the sensor 44 and connecting tubes 46, 48. In the preferred embodiment, the flow sensor 44 is the aforementioned transducer manufactured by Microswitch Corp., Model AWM2300V. The side flow is proportional to the total flow through the conduit 34. The sensor 44 produces an electrical signal representative of that total flow.

In an alternative embodiment (not shown) the flow sensor 44 is replaced with a differential pressure sensor, such as the Microswitch Corp., Model 24EFA1D differential pressure sensor. The differential pressure sensor measures a pressure drop proportional to flow velocity and thus to the total flow of gas through the flow conduit 34. With this arrangement, there is no side flow through the connecting tubes 46, 48.

Both of the sense tubes 36, 40 are identical in construction. The construction of the upstream sense tube 36 is shown in detail in FIGS. 6-9.

In the preferred embodiment, as shown in FIGS. 6-9, the sense tube 36 is a machined tube preferably formed of stainless steel material with a 0.093" outside diameter and a 0.010" wall thickness. A passivate finish is applied.

A semi-cylindrical notch opening 38 is formed on both ends of the tube 36. Preferably, both notches are identical in size and shape and face in the same direction. In a preferred embodiment, the tube 36 has an overall length of about 1,160" and each notch has a length of about 150" leaving about 860" of tubing between the two notches. The depth of each notch 36 is slightly less than half the diameter of the tube 36, or about 0.046" in the preferred embodiment.

The particular end geometries were selected to produce high drag coefficient values when immersed in turbulent flow, thereby resulting in a large pressure differential between the two sense tubes 36, 40 and a large side flow through the sensor 44.

In the case of the upstream notch opening 38 directed into the flow, a large drag coefficient produces a high pressure area where the flow impacts the tube 36. The upstream sense tube 36 opens into this area of the flow and transmits the higher pressure to the input side of the sensor 44. In the case of the notch opening 42, directed away from the flow, maximum flow separation occurs on the downstream side of the notch 42. This flow separation creates a low pressure area. The downstream sense tube 40 opens into this area and transmit the lower pressure to the output side of the sensor 44. The combination of high pressure at the sensor input and low pressure at the sensor output produces a large side flow, resulting in a high flow signal through the sensor 44.

A semi-cylindrical shape is known to provide a large difference in drag coefficient depending upon whether it is oriented in an upstream facing or downstream facing manner. Thus, the notch in the tubes 36, 40, as shown in FIGS. 6-9, provides a substantial pressure differential, resulting in an optimized flow signal to the sensor 44.

The dimensional characteristics of the notched tube give stability to the differential pressure developed by the conduit flow, resulting in a low noise signal in a turbulent flow environment. The sensor signal (i.e., the side flow) could be altered by changing the size and possibly the height-to-width ratio of the notches, but the particular size described herein provides optimum sensitivity and range for the applicant's particular respirator application, described below.

The notched tube also is relatively easy to manufacture. The ability to use the same tube configuration for both the upstream and downstream sense tubes 36, 40 allows economic purchasing quantities and minimizes potential assembly errors. The tubes are notched on both ends to facilitate the manufacturing process and also to give visibility to the notch position and orientation during assembly. If desired, the notch on the external end of the sense tube could be eliminated.

The distance between the upstream sense tube 36 and the downstream sense tube 40 in the flow conduit 34 is not critical. However, the tubes 36, 40 should be sufficiently separated to allow flow to develop around the downstream tube thus generating flow separation effects and the resulting pressure difference between the two tubes 36, 40.

The flow measuring device 32 is particularly well suited for taking accurate measurements in turbulent flow, due to the location in the middle of the flow stream and the averaging effects of the tube notch openings 38, 42.

Referring to FIGS. 10 and 11, a second embodiment of the flow measuring device 50 is shown. It is similar to the flow measuring device 32 of FIGS. 2-4 and operates in a similar fashion. The device 50 of FIGS. 10 and 11 has been designed specifically for use in the Puritan-Bennett Companion 320I/E Bi-Level Respiratory System.

As shown in FIGS. 10 and 11, the flow measuring device 50 includes an angled flow conduit 52 having a first cylindrical section 54 and a second cylindrical section 56 oriented at an angle with respect to the first section 54. In the preferred embodiment, the angle is about 14.5 degrees. The purpose of the angle is to fit the device 50 in the desired enclosure.

The flow measuring device 50 utilizes upstream 58 and downstream 60 sense tubes which are identical in construction to the sense tube 36 shown and described in FIGS. 6-9. The upstream sense tube 58 extends through a first sidewall tap at the junction between the first 54 and second 56 cylindrical sections. The downstream sense tube 60 is received through a second sidewall tap in the first cylindrical section 54. The internal ends of both sense tubes 58, 60 protrude into the flow stream through the conduit 52. The notch openings on the internal ends of the sense tubes 58, 60 are located in approximately the middle of the flow stream, with the downstream sense tube 60 being oriented so that its notch opening faces directly downstream in the first cylindrical section 54 and the upstream sense tube 58 being oriented so that its notch opening faces directly upstream in the second cylindrical section 56. The distance between the two sense tubes 58, 60 is not critical, so long as there is sufficient spacing between them to produce flow separation effects and the resulting pressure difference between the two tubes 36, 40. The external ends of both sense tubes 58, 60 are connected through connecting tubes (not shown) to a flow sensor (not shown) in a manner identical to that shown in FIG. 2.

In the preferred application, the first cylindrical section 54 serves as an outlet connector for the pneumatic hose 20 of FIG. 1. The second cylindrical section 56 serves as a connector to the outlet port of the valve assembly 14.

As shown in FIG. 11, the first cylindrical section 54 also is provided with a sidewall tap 62 opposite the downstream sense tube 60. A nipple connector 64 is formed on the outer surface of the section 54 around the tap 62 for connection to a PVC connecting tube (not shown). In the preferred embodiment, the connecting tube is joined to a pressure tube which communicates with the inlet side of the pressure sensor 16. Using this configuration, the flow measuring device 50 provides input both to the pressure sensor 16 and to the flow sensor 18 in the respirator system of FIG. 1.

From the foregoing, it will be appreciated that the flow measuring apparatus of the present invention provides accurate measurements of total flow in a turbulent or pulsating environment such as a respirator system, and does so with a high signal-to noise ratio. Further, the flow measuring apparatus provides a symmetrical design which is capable of operating with flow in either direction.

While several particular forms of the invention have been illustrated and described, it will be apparent that various modifications can be made without departing from the spirit and scope of the invention. Accordingly, it is not intended that the invention be limited, except as by the appended claims.

We claim:

1. Flow measuring apparatus, comprising:
   a flow conduit;
   an upstream sense tube having a notch opening disposed in the flow conduit and facing into a flow stream through said flow conduit;
   a downstream sense tube having a notch opening disposed in the flow conduit and facing away from the flow stream; and
   a transducer operatively connected to the upstream and downstream sense tubes for receiving a signal therefrom.

2. Apparatus as set forth in claim 1, wherein said transducer comprises a flow sensor.

3. Apparatus as set forth in claim 1, wherein said transducer comprises a differential pressure sensor.

4. Apparatus as set forth in claim 1, wherein said flow conduit is a straight conduit.

5. Apparatus as set forth in claim 1, wherein said flow conduit is an angled conduit.

6. Apparatus as set forth in claim 1, wherein said upstream and downstream sense tubes have notch openings on both ends thereof.

7. Apparatus as set forth in claim 1, wherein said notch openings are disposed in about a center of the flow stream in said flow conduit.

8. Flow measuring apparatus, comprising:
   a flow conduit;
   an upstream sense tube having a notch opening disposed in the flow conduit and facing into a flow stream through said flow conduit;
   a downstream sense tube having a notch opening disposed in the flow conduit and facing away from the flow stream; and
   a transducer operatively connected to the upstream and downstream sense tubes for receiving a signal therefrom, wherein said notch openings have a semi-cylindrical shape.

9. Apparatus as set forth in claim 8, wherein said notch openings have a longitudinal length approximately equal to one and a half times a diameter of said respective sense tubes.

10. Apparatus as set forth in claim 9, wherein said notch openings have a longitudinal length of about 0.150" and a depth of about 0.046".

11. Flow measuring apparatus, comprising:
    a flow conduit;
    an upstream sense tube having a notch opening disposed in the flow conduit and facing into a flow stream through said flow conduit;
    a downstream sense tube having a notch opening disposed in the flow conduit and facing away from the flow stream; and
    a transducer operatively connected to the upstream and downstream sense tubes for receiving a signal therefrom, wherein said upstream and downstream sense tubes have notch openings on both ends thereof, wherein said notch openings are of identical size and shape.

12. Flow measuring apparatus, comprising:
    a flow conduit;
    an upstream sense tube having a notch opening disposed in the flow conduit and facing into a flow stream through said flow conduit;
    a downstream sense tube having a notch opening disposed in the flow conduit and facing away from the flow stream; and
    a transducer operatively connected to the upstream and downstream sense tubes for receiving a signal therefrom, wherein each of said upstream and downstream sense tubes has an internal portion disposed in said flow conduit and an external portion disposed outside of said flow conduit, each of said internal and external portions having a notch opening formed in an end thereof.

13. Apparatus as set forth in claim 12, wherein each of said upstream and downstream sense tubes has said notch opening in said external portion identically oriented as said notch opening in said internal portion relative to said flow stream.

14. Flow measuring apparatus, comprising:
    a flow conduit;
    a sense tube with a notch opening disposed in the flow conduit in a flow stream through said flow conduit; and
    a transducer operatively connected to the sense tube for receiving a signal therefrom.

15. Apparatus as set forth in claim 14, wherein said notch opening is disposed in about a middle of the flow stream.

16. Flow measuring apparatus, comprising:
    a flow conduit;

a sense tube with a notch opening disposed in the flow conduit in a flow stream through said flow conduit; and a transducer operatively connected to the sense tube for receiving a signal therefrom, wherein said notch opening has a semi-cylindrical shape.

17. Flow measuring apparatus, comprising:

a flow conduit;

a sense tube with a notch opening disposed in the flow conduit in a flow stream through said flow conduit; and a transducer operatively connected to the sense tube for receiving a signal therefrom, wherein said notch opening has a longitudinal length approximately equal to a one and a half times diameter of said sense tube.

18. Flow measuring apparatus, comprising:

a flow conduit;

a sense tube with a notch opening disposed in the flow conduit in a flow stream through said flow conduit; and a transducer operatively connected to the sense tube for receiving a signal therefrom, wherein said notch opening has a longitudinal length of about 0.150" and a depth of about 0.046".

* * * * *

UNITED STATES PATENT AND TRADEMARK OFFICE
CERTIFICATE OF CORRECTION

PATENT NO. : 5,443,075
DATED : August 22, 1995
INVENTOR(S) : Russell L. Holscher It is certified that error appears in the above-indentified patent and that said Letters Patent is hereby corrected as shown below:

Column 5, line 49, change "1,160" to --1.160--.
Column 5, line 50, change "150" to --0.150--.
Column 5, line 50, change "860" to --0.860--.

Signed and Sealed this

Twentieth Day of August, 1996

Attest:

BRUCE LEHMAN

Attesting Officer          Commissioner of Patents and Trademarks